United States Patent
Tran (10) Patent No.: US 12,144,943 B2
(45) Date of Patent: Nov. 19, 2024

(54) ENHANCED GUIDE WIRE ADVANCEMENT LENGTH

(71) Applicant: Bard Access Systems, Inc., Salt Lake City, UT (US)

(72) Inventor: Huy N. Tran, Riverton, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 423 days.

(21) Appl. No.: 17/313,901

(22) Filed: May 6, 2021

(65) Prior Publication Data

US 2021/0346655 A1 Nov. 11, 2021

Related U.S. Application Data

(60) Provisional application No. 63/021,502, filed on May 7, 2020.

(51) Int. Cl.
*A61M 25/09* (2006.01)
*A61M 25/01* (2006.01)

(52) U.S. Cl.
CPC .. *A61M 25/09041* (2013.01); *A61M 25/0133* (2013.01); *A61M 2025/09066* (2013.01)

(58) Field of Classification Search
CPC ........ A61M 25/09041; A61M 25/0133; A61M 25/0113; A61M 25/09; A61M 2025/09066; A61M 2025/09116; A61M 2025/09091
See application file for complete search history.

(56) References Cited

U.S. PATENT DOCUMENTS

| | | | |
|---|---|---|---|
| 8,932,258 B2 | 1/2015 | Blanchard et al. | |
| 9,872,971 B2 | 1/2018 | Blanchard | |
| 9,950,139 B2 | 4/2018 | Blanchard et al. | |
| 10,384,039 B2 | 8/2019 | Ribelin et al. | |
| 2005/0197663 A1* | 9/2005 | Soma ............... | A61M 25/09041 606/108 |
| 2011/0282285 A1 | 11/2011 | Blanchard et al. | |
| 2012/0197200 A1 | 8/2012 | Belson | |
| 2014/0094774 A1 | 4/2014 | Blanchard | |
| 2014/0276436 A1* | 9/2014 | Lafitte ............... | A61M 25/0662 604/164.13 |
| 2020/0016374 A1* | 1/2020 | Burkholz .......... | A61M 25/0606 |

FOREIGN PATENT DOCUMENTS

WO 2007/006055 A2 1/2007

OTHER PUBLICATIONS

PCT/US2021/031164 filed May 6, 2021 International Search Report and Written Opinion dated Nov. 5, 2021.

* cited by examiner

*Primary Examiner* — Laura A Bouchelle
*Assistant Examiner* — Sarah Dympna Grasmeder
(74) *Attorney, Agent, or Firm* — Rutan & Tucker LLP (57) ABSTRACT

Systems and methods for extending a guidewire from an insertion tool are disclosed. A guidewire assembly includes a slider configured to engage a guidewire carrier. The guidewire carrier defines a lumen configured to receive a guidewire therein. The guidewire carrier is biased to a non-linear, coiled resting state and can elastically transition to a linear extended state. As the guidewire assembly and slider are urged distally, the slider transitions the guidewire carrier from the non-linear state to the linear extended state. A distance travelled by the slider is less than a distance travelled by a tip of the guidewire as the guidewire carrier transitions from the coiled state to the linear state.

21 Claims, 9 Drawing Sheets

ENHANCED GUIDE WIRE ADVANCEMENT LENGTH

PRIORITY

This application claims the benefit of priority to U.S. Provisional Application No. 63/021,502, filed May 7, 2020, which is incorporated by reference in its entirety into this application.

SUMMARY

Briefly summarized, embodiments disclosed herein are directed to guidewire advancement systems and methods thereof.

Disclosed herein is a system for advancing a guidewire from an insertion tool including, a guidewire advancement assembly slidably engaged with the insertion tool and configured to transition between a proximal position and a distal position, the guidewire advancement assembly including, a slider defining a slider channel, and a guidewire carrier defining a lumen configured to receive a guidewire therethrough, the guidewire carrier defining a non-linear resting state, and wherein the slider channel is configured to receive the guidewire carrier and transition the guidewire carrier from the non-linear resting state to a linear extended state as the guidewire advancement assembly transitions from a proximal position to a distal position.

In some embodiments, the non-linear resting state includes one of a serpentine coil shape, coiled, folded, or helical. The guidewire carrier is biased to the non-linear resting state and is formed of one of a plastic, polymer, elastomer, rubber, silicone, metal, alloy, or nitinol. The non-linear resting state includes one or more coils extending perpendicular from a longitudinal axis, and wherein a longitudinal length of the slider is greater than a longitudinal length of a coil of the one or more coils. A first distance ("a") that is traveled by the slider as the guidewire advancement assembly transitions between the proximal positon and the distal position, is less than a second distance ("b") that is traveled by a tip of the guidewire as the guidewire carrier transitions between the non-linear resting state and the linear extended state. The relationship between the first distance ("a") and the second distance ("b") is expressed as:

$$= \pi\sqrt{\frac{a^2 + b^2}{2}}$$

In some embodiments the guidewire carrier defines a substantially circular cross-sectional shape and includes a left rail and a right rail extending laterally therefrom. The slider channel defines a left recess configured to engage the left rail of the guidewire carrier, and defines a right recess configured to engage the right rail of the guidewire carrier. The guidewire carrier engages the slider channel in a friction fit engagement. One of the guidewire carrier and the guidewire is coupled to a proximal end of the insertion tool. One of a proximal end of the guidewire carrier or a proximal end of the guidewire remains in a longitudinally fixed position relative to the insertion tool.

Also disclosed is a method of extending a guidewire from an insertion tool including, providing a guidewire advancement assembly transitionable between a proximal position and a distal position, and including a slider defining a channel, and a guidewire carrier engaged with the slider channel, and defining a lumen configured to receive a guidewire therein, the guidewire carrier biased to a non-linear resting state, advancing the guidewire advancement assembly from the proximal position to the distal position, sliding the slider along an outer surface of the guidewire carrier, transitioning the guidewire carrier from the non-linear resting state to an extended state, and advancing a tip of the guidewire in a distal direction.

In some embodiments, the non-linear resting state includes one of a serpentine coil shape, coiled, folded, or helical. The guidewire carrier is elastically deformable and includes one of a plastic, polymer, elastomer, rubber, silicone, metal, alloy, or nitinol material. A first distance ("a") that is traveled by the slider as the guidewire advancement assembly transitions between the proximal positon and the distal position, is less than a second distance ("b") that is traveled by the tip of the guidewire. The relationship between the first distance ("a") and the second distance ("b") is expressed as:

$$= \pi\sqrt{\frac{a^2 + b^2}{2}}$$

In some embodiments, the guidewire carrier defines a substantially circular cross-sectional shape and includes a left rail and a right rail extending laterally therefrom. The slider channel defines a left recess configured to engage the left rail of the guidewire carrier, and defines a right recess configured to engage the right rail of the guidewire carrier. The guidewire carrier engages the slider channel in a friction fit engagement. One of the guidewire carrier and the guidewire is coupled to a proximal end of the insertion tool. A proximal end of the guidewire carrier or a proximal end of the guidewire remains in a longitudinally fixed position relative to the insertion tool.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which.

DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

Figure 1A:
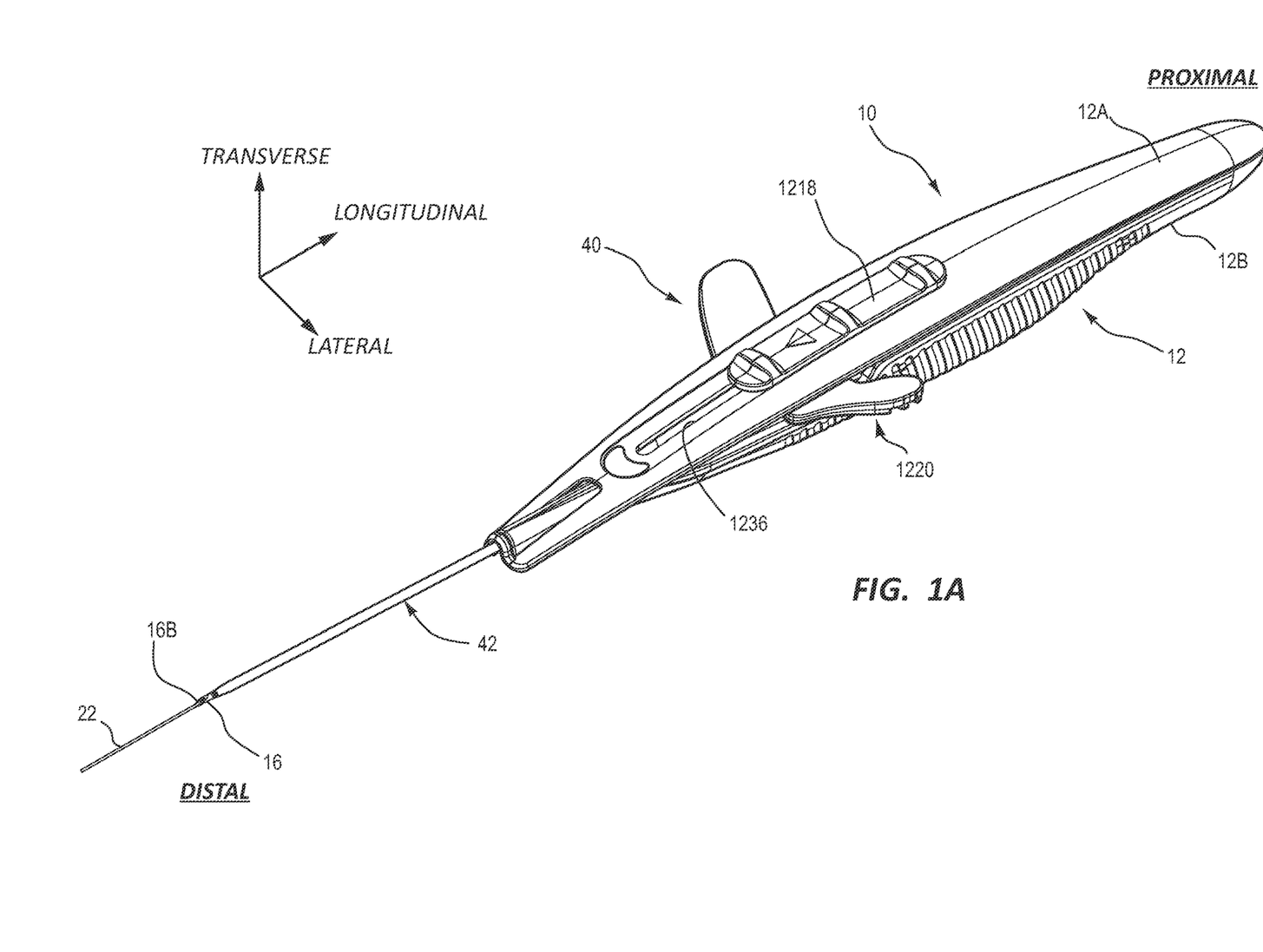
FIGS. 1A-1F show various views of a catheter insertion tool, in accordance with embodiments disclosed herein.
Figure 1B:
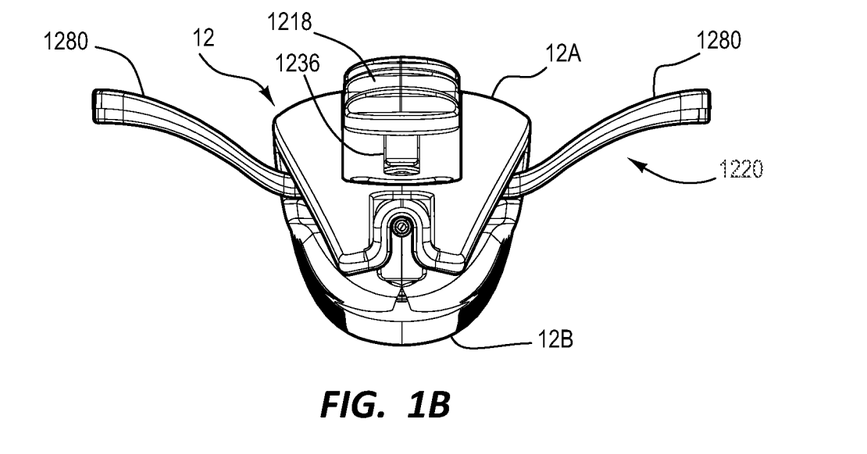
Figure 1C:
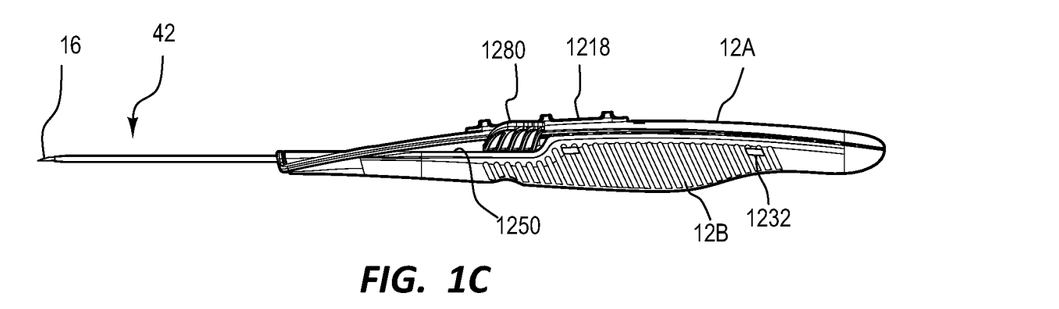
Figure 1D:
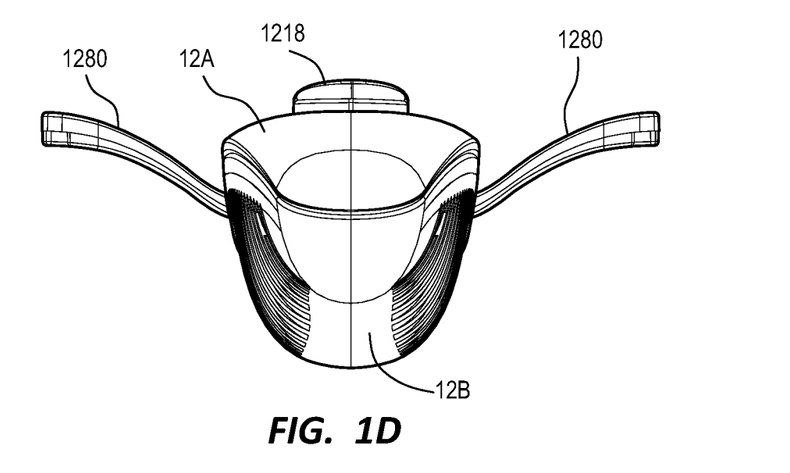
Figure 1E:
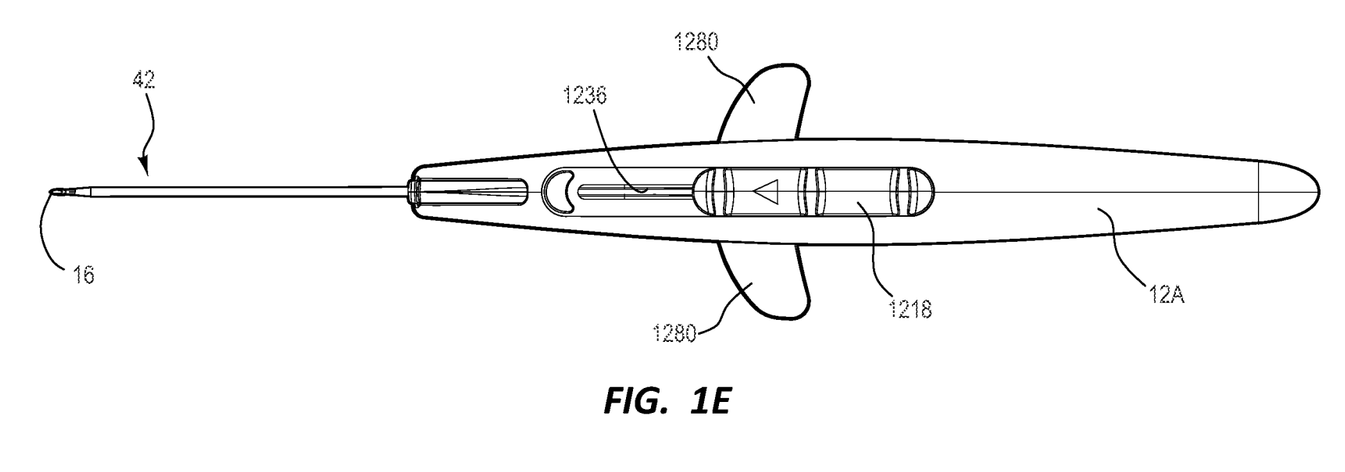
Figure 1F:
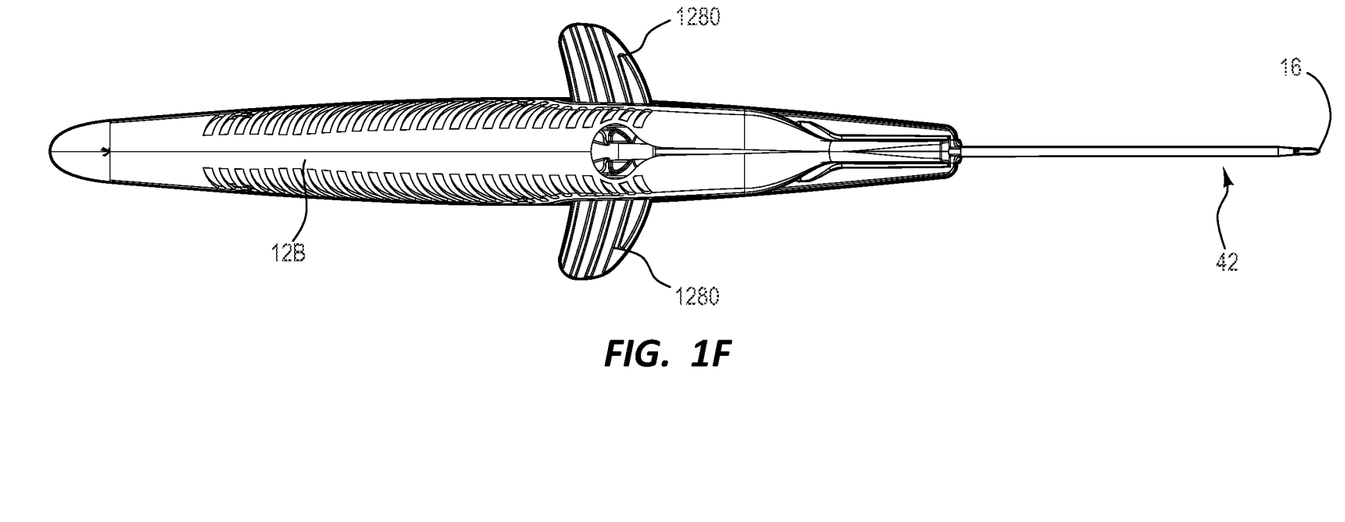

To assist in the description of embodiments described herein, as shown in FIG. 1A, a longitudinal axis extends substantially parallel to an axial length of a guidewire 22. A lateral axis extends normal to the longitudinal axis, and a transverse axis extends normal to both the longitudinal and lateral axes.

Unless defined otherwise, all technical and scientific terms used herein have the same meaning as commonly understood by those of ordinary skill in the art.

Briefly summarized, embodiments herein are generally directed to an insertion tool for inserting a catheter or other tubular medical device into a body of a patient. The insertion tool in one embodiment unifies needle insertion, guidewire advancement, and catheter insertion in a single device to provide for a simple catheter placement procedure. The insertion tool further includes a multiplier wherein a single unit of guidewire assembly advancement provides greater than one unit of guidewire advancement from the insertion tool.

Figure 2:
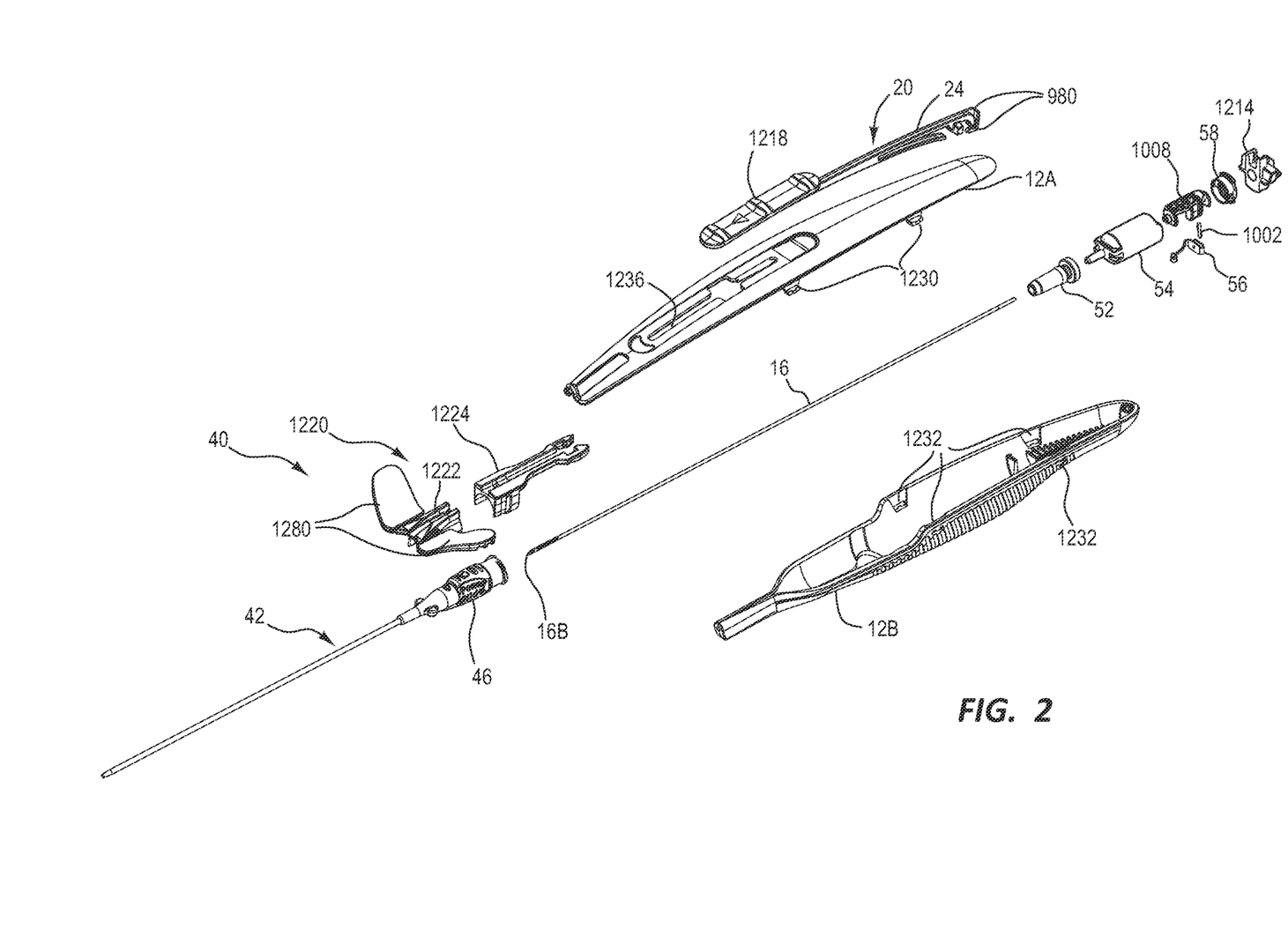
FIG. 2 shows an exploded view of the insertion tool of FIG. 1A, in accordance with embodiments disclosed herein.

FIGS. 1A-1F and 2 depict various details of an exemplary insertion tool 10 according to embodiments disclosed herein. As shown in FIGS. 1A and 2, the insertion tool 10 includes the top and bottom housing portions 12A, 12B of the housing 12, from which extends the catheter 42 disposed over the needle 16. Also shown in FIG. 1A is a finger pad 1218 of the guidewire advancement assembly 20 slidably disposed in a slot 1236 defined in the top housing portion 12A, together with a portion of a handle assembly 1220 of the catheter advancement assembly 40. Further details and embodiments of the exemplary insertion tool 10 can be found in U.S. Pat. Nos. 8,932,258, 9,872,971, 9,950,139, and U.S. Pat. No. 10,384,039, each of which is hereby incorporated by reference in their entirety.

FIGS. 1A-1F show the finger pad 1218 as part of the guidewire advancement assembly 20 and can be slid by a finger(s) of the clinician distally along the slot 1236 in order to enable selective advancement of the guidewire 22 (initially disposed within the lumen of the needle 16) out past the distal end 16B of the needle 16. In an embodiment, a proximal end of the guidewire 22 can be attached to a proximal portion of the housing 12. In an embodiment, the insertion tool 10 can include a one or more guidewire advancement multiplier mechanisms. For example, a multiplier advancement mechanism can include a proximal end of the guidewire 22 attached to an interior portion of the top housing portion A such that a single unit of distal sliding advancement of the finger pad 1218 results in two units of distal guidewire advancement. This can be made possible by looping the guidewire 22 from its attachment point on the top housing portion 12A and through the guide surfaces 980 included on the guidewire lever 24 before extending into the lumen of the needle 16. Further details of the "looped" guidewire advancement multiplier mechanisms can be found in U.S. Pat. Nos. 9,872,971, 9,950,139, and U.S. Pat.

No. 10,384,039, each of which is hereby incorporated by reference in its entirety into this application.

In an embodiment, a "guidewire carrier" multiplier advancement mechanism can include a guidewire 22 disposed within a guidewire carrier 440 that defines a non-linear, coiled shape. Advancing the guidewire assembly 20 can restrict the guidewire carrier to a linear shape such that a single unit of distal sliding advancement of the finger pad 1218 results in greater than one unit of distal guidewire advancement, as describe in more detail herein. In an embodiment, an insertion tool 10 can include both the "looped" guidewire advancement multiplier mechanism, as well as the "guidewire carrier" advancement mechanism, or features thereof, to provide a compounded advancement multiplication factor through simultaneously using both guidewire advancement mechanisms. It will be appreciated that additional guidewire multiplier advancement mechanisms can be used in place of or in addition to the guidewire multiplier advancement mechanisms described herein. In an embodiment the guidewire lever 24 and finger pad 1218 of the guidewire advancement assembly 20 can be integrally formed with one another, though they may be separately formed in other embodiments. Note also that the guidewire 22 can be attached to other external or internal portions of the insertion tool 10, including the bottom housing portion 12B, the needle hub 1214, etc.

FIGS. 1A-1F further show a catheter advancement assembly 40 for selectively advancing the catheter 42 in a distal direction out from the housing 12 of the insertion tool 10. The catheter advancement assembly 40 includes a handle assembly 1220, which in turn includes among other components two wings 1280 that are grasped by the fingers of the clinician when the catheter is to be advanced. The wings 1280 distally advanced via the gap 1250 defined between the top and bottom housing portions 12A, 12B.

The exploded view of the insertion tool 10 in FIG. 2 shows that the handle assembly 1220 includes a head portion 1222 from which extend the wings 1280, and a tail portion 1224. Both the head portion 1222 and the tail portion 1224 are removably attached to the catheter hub 46. Internal components of the insertion tool 10 that are disposed within the housing 12, each of which is passed through by the needle 16 include valve 52, a safety housing 54 in which the carriage 1008 and the needle safety component 56 is disposed, and a cap 58 of the safety housing. An O-ring 1002 is included with the needle safety component 56 is also shown, as is a needle hub 1214, which is secured to a proximal end of the needle 16 and is mounted to the housing 12 to secure the needle 16 in place within the insertion tool 10. Note in FIG. 2 that, in one embodiment, the slot 1236 in which the finger pad of the guidewire advancement assembly 20 is disposed includes a relatively wide portion to enable the guidewire lever 24 to be inserted therethrough in order to couple the guidewire advancement assembly to the housing 12.

FIGS. 3A-4B, show further details of an embodiment of a guidewire advancement assembly 20. The guidewire advancement assembly 20 can include a slider 330 extending from a distal end 330B to a proximal end 330C and configured to engage a guidewire carrier 440 disposed within the housing 12 of the insertion tool 10. The guidewire carrier 440 can extend from a distal end 440B to a proximal end 440C, and can define a guidewire carrier lumen 442 extending longitudinally and configured to receive a guidewire 22 extending therethrough.

Figure 3A:
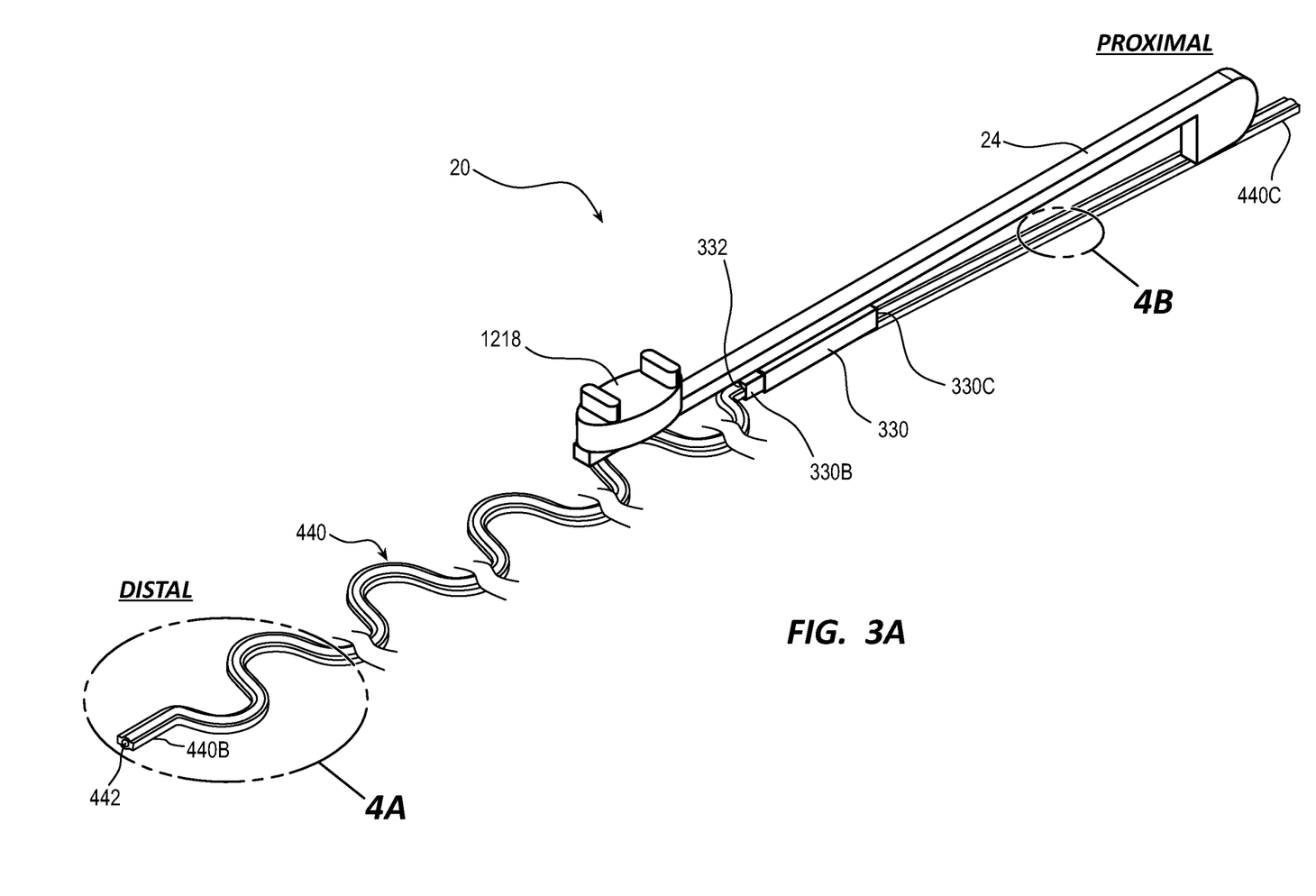
FIG. 3A shows an exploded perspective view of a catheter advancement assembly including a guidewire carrier and a guidewire, in accordance with embodiments disclosed herein.
Figure 4A:
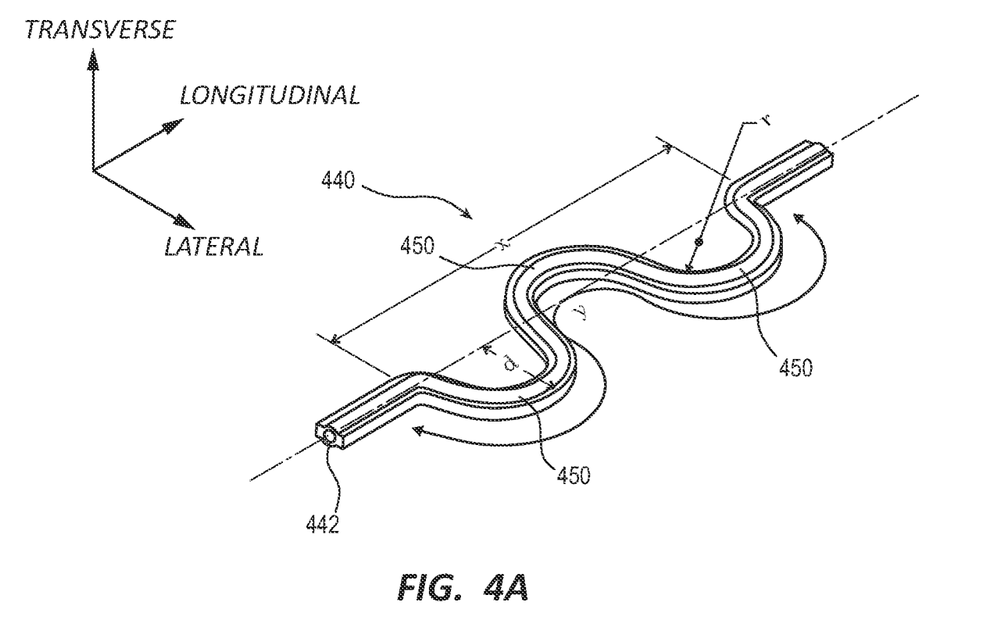
FIG. 4A shows a perspective view of a guidewire carrier in a non-linear state, in accordance with embodiments disclosed herein.
Figure 4B:
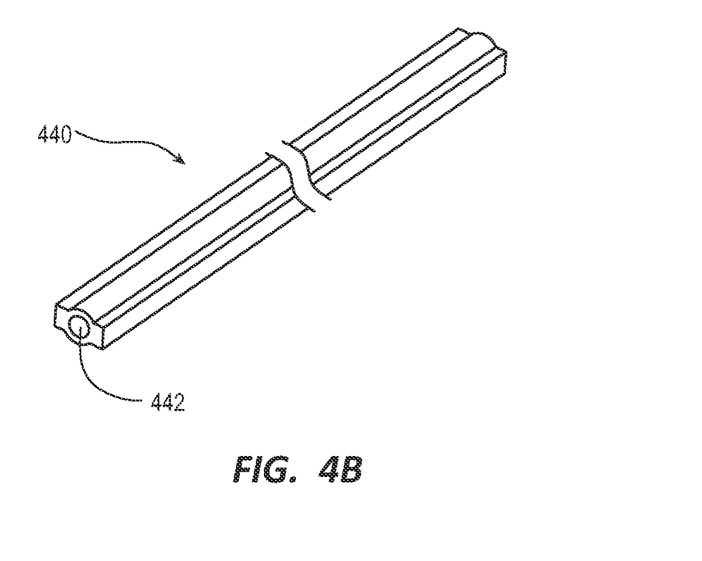
FIG. 4B shows a perspective view of a guidewire carrier in a linear state, in accordance with embodiments disclosed herein.

In an embodiment, the guidewire carrier 440 can define a non-linear shape, for example a serpentine coil shape as shown in FIGS. 3A and 4A. In an embodiment, the guidewire carrier 440 can be formed of a flexible material, for example plastic, polymer, elastomer, rubber, silicone, metal, alloy, nitinol, combinations thereof, or the like. The guidewire carrier 440 can be biased towards the non-linear state (FIG. 4A), such that at rest, the guidewire carrier 440 resumes the non-linear state. In an embodiment, the guidewire carrier 440 can be elastically deformable from the non-linear resting state to a linear extended state (FIG. 4B). The guidewire carrier 440 can then resume the non-linear resting state when the deforming force is removed.

FIG. 4A shows further details of an embodiment of a non-linear configuration, for example a serpentine coil shape extending along a horizontal plane. Each coil 450 can extend laterally from a central longitudinal axis. Each adjacent coil can extend laterally in an opposite direction from the previous coil to define the serpentine shape. An apex of the coil 450 can extend laterally from a central longitudinal axis by a distance (d). As such, the guidewire carrier can extend laterally by a distance of (2d). A radius of curvature (r) of the apex of each coil can also vary. For example, for a given longitudinal distance (x), a smaller radius of curvature (r) will provide a greater number of coils 450 contained within the distance (x). As such, the greater the distance (d), the smaller the radius of curvature (r), or combinations thereof, the greater the overall length (y) of the guidewire carrier 440 can fit within a given longitude distance (x).

While coils extending along the lateral axis are shown, it will be appreciated that this is a simplified illustration and coils extending along the lateral axis, transverse axis, axes disposed at an angle therebetween, or combinations thereof, are also contemplated to fall within the scope of the present invention. Further, adjacent coils can define the same lateral distance (d), the same radius of curvature (r), or different lateral distances (d) or radii of curvature (r), or combinations thereof. Further, it will be appreciated that other non-linear configurations are also contemplated, for example the guidewire carrier can include coiled, folded, helical, or combinations thereof, and the like and still fall within the scope of the present invention.

Figure 3B:
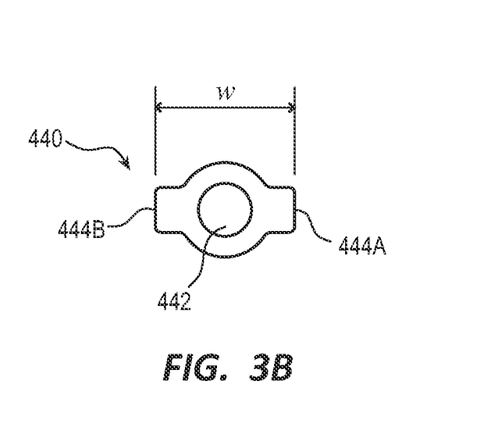
FIG. 3B shows cross-sectional view of a guidewire carrier, in accordance with embodiments disclosed herein.
Figure 3C:
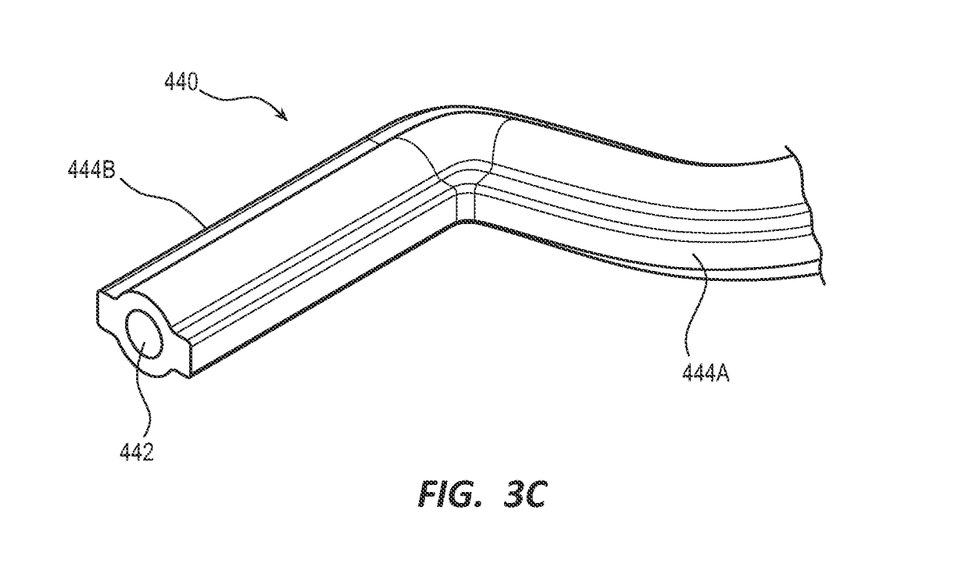
FIG. 3C shows a cross-sectional perspective view of a guidewire carrier, in accordance with embodiments disclosed herein.
Figure 3D:
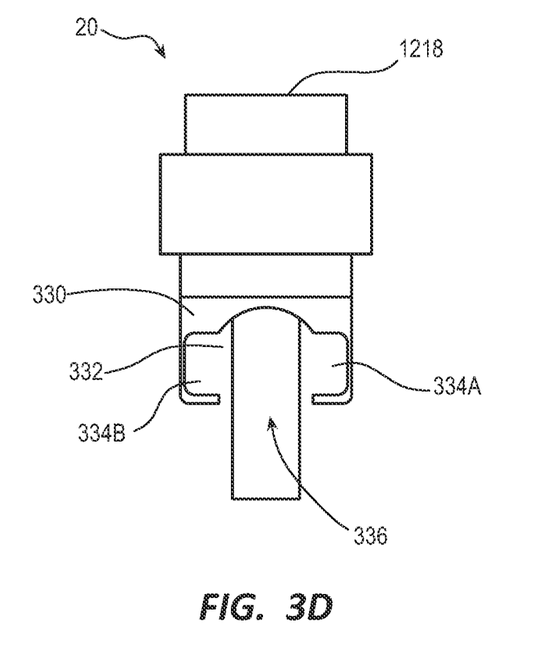
FIG. 3D shows a front view of a guidewire advancement assembly, in accordance with embodiments disclosed herein.
Figure 3E:
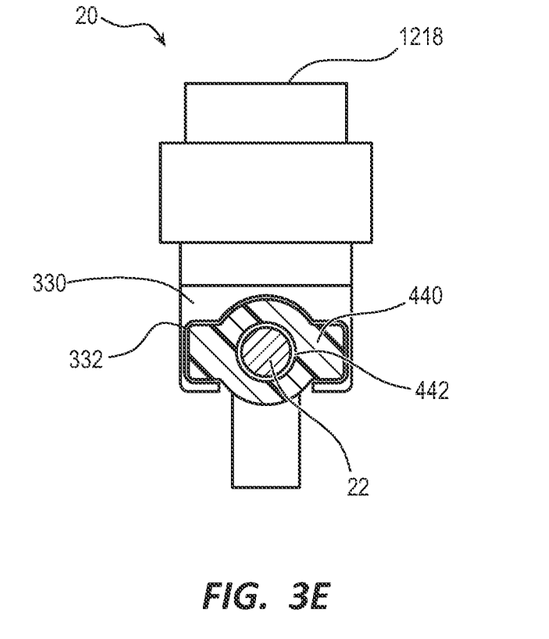
FIG. 3E shows a front view of a catheter advancement assembly including a guidewire carrier and a guidewire, in accordance with embodiments disclosed herein.

As shown in FIGS. 3B-3E, in an embodiment, the slider 330 can be configured to engage the guidewire carrier 440. The slider 330 can define a channel 332 configured to receive the guidewire carrier 440 therethrough. As shown in FIGS. 3B-3C, a cross-sectional shape of the guidewire carrier 440 defines a substantially circular cross-section and includes one or more rectangular rails extending laterally from a side surface, for example a left rail 444A and a right rail 444B. It will be appreciated, that other cross-sectional shapes are also considered to fall within the scope of the present invention. As shown in FIGS. 3B and 3E, the left rail 444A can be configured to engage a left recess 334A of the slider channel 332, the right rail 444B can be configured to engage a right recess 334B of the slider channel 332. In an embodiment, the slider 330 can include a longitudinal opening 336 dispose on a lower side of the slider and communicating with the slider channel 332. The opening 336 can facilitate ingress/egress of the guidewire carrier 440, and guidewire 22 disposed therein, during manufacture and assembly. Further, the opening 336 can facilitate the operation of other guidewire advancement multiplier mechanisms, e.g. the "looped" guidewire advancement multiplier mechanism, as described herein. As noted herein, using two or more guidewire advancement multiplier mechanisms can provide a compounded multiplication effect.

In an embodiment, the lateral width of the channel 332 can be substantially the same as a lateral width (w) of the cross-sectional shape of the guidewire carrier 440. A longitudinal length of the slider 330 can be greater than a longitudinal length of at least one coil 450. In an embodiment, a longitudinal length of the slider 330 can be greater than a longitudinal length of a plurality of coils, e.g. distance (x). As such, the slider channel 332 can restrict the lateral extension of one or more coils 450 of the guidewire carrier 440.

Figure 5A:
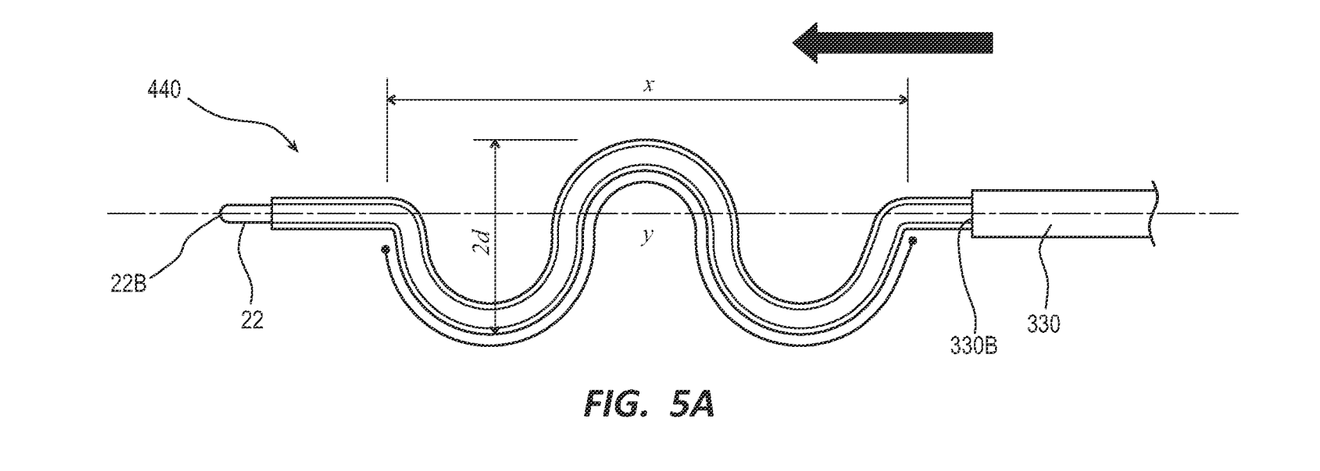
FIG. 5A shows a plan view of a guidewire carrier in a non-linear state, in accordance with embodiments disclosed herein.
Figure 5B:
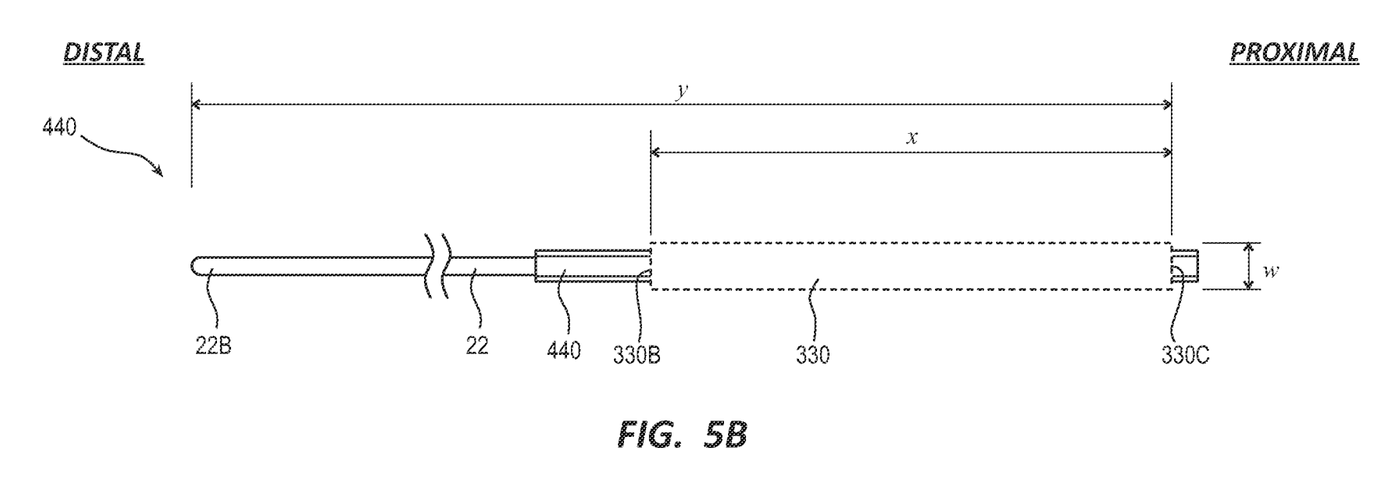
FIG. 5B shows a plan view of a guidewire carrier in a linear state, in accordance with embodiments disclosed herein.

As shown in FIGS. 5A-5B, in an exemplary method of use, the slider 330 of the catheter assembly 20 engages a portion of the guidewire carrier 440 with the guidewire 22 disposed therethrough. In an embodiment, a proximal end 440C of the guidewire carrier 440 and, optionally, the guidewire 22, can be coupled to a proximal portion of the insertion tool housing 12. As such, a proximal end of the guidewire carrier 440/guidewire 22 assembly remains in a fixed position relative to the insertion tool 10. In an embodiment, the guidewire 22, guidewire carrier 440, or combinations thereof can be looped around a proximal end of the guidewire lever 24 and attached to a portion of the housing 12, as described herein. As such the insertion tool 10 can employ a combination of guidewire advancement multiplier mechanisms to advance the guidewire 22.

The guidewire advancement assembly 20 can be urged distally by a user advancing the finger pad 1218 distally through slot 1236. As the slider 330 travels from a proximal end to a distal end, the slider 330 transitions the guidewire carrier 440 from the non-linear state (FIG. 5A) to the extended linear state (FIG. 5B). For example, as the slider 330 advances distally the slider 330 engages the guidewire carrier 440 and restricts the lateral extension of one or more coils 450. As the slider 330 continues to advance distally additional coils are similarly laterally restricted (FIG. 5B). As such, a length of guidewire carrier (y) that was previously contained within a given longitudinal distance (x) in a coiled resting state (FIG. 5A), is now extended distally in the extended, non-linear state (FIG. 5B). A portion of guidewire 22 disposed within the guidewire carrier 440 is similarly transitioned from a non-linear configuration to an extended linear configuration and a distal tip 22B of the guidewire 22 extends distally.

Advantageously, the guidewire carrier 440 and slider 330 provides a multiplier effect wherein one unit of distal advancement of the guidewire assembly 20 provides a greater than one unit of distal extension of the guidewire tip 22B. More specifically, the ratio of guidewire assembly 20 movement to advancement of the guidewire tip 22B can be expressed as:

$$= \pi \sqrt{\frac{a^2 + b^2}{2}}$$

where "a" is the minor axis length of the non-linear path and "b" is the major axis length of the non-linear path. The slider 330 can extend along the minor axis ("a"), substantially a distance (x), whereas the guidewire tip 22B can extend distally along the major axis ("b"), substantially a length (y). As previously noted, the greater the distance (d), the smaller the radius of curvature (r), or combinations thereof, the greater the major axis "b", is relative to the minor axis "a" and the greater the multiplier effect for advancing the guidewire tip 22B.

Advantageously, the multiplier mechanism allows the length of the insertion tool 10 to remain the same while allowing for a greater length of guidewire 22 to be stored therein and extended therefrom. Worded differently, a relatively more compact insertion tool 10 can be provided while still providing a similar length of guidewire 22 to be stored therein.

In an embodiment, the slider 330 engages the guidewire carrier 440 in a frictional fit. As shown in FIG. 3A, while the portion of the guidewire carrier 440 disposed within the slider channel 332 is compressed to a linear state, a proximal portion of guidewire carrier 440 disposed between a proximal end 330C of the slider 330 and the proximal end 440C of the guidewire carrier 440 also remains in the linear configuration. The proximal portion of the guidewire carrier 440 is unable to return to the non-linear configuration since it is stretched between the slider 330 and the proximal end of the insertion tool 10. When the guidewire assembly 20 is disposed at a distal-most position within the slot 1236, the slider 330 maintains the entire guidewire carrier 440 in the linear, extended state.

It will also be appreciated that the guidewire 22 can also be retracted in a similar manner. The guidewire assembly 20 can be urged from the distal-most position within the slot 1236 to the proximal-most position. The slider 330 retracts proximally along the guidewire carrier 440 and removes the deforming force from the guidewire carrier 440. The guidewire carrier 440 transitions from the linear state to the non-linear resting state and retracts the guidewire 22 back into the guidewire carrier lumen 332.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A system for advancing a guidewire from an insertion tool, comprising:
    a guidewire advancement assembly slidably engaged with the insertion tool and configured to transition between a proximal position and a distal position, the guidewire advancement assembly comprising:
    a slider defining a slider channel; and
    a guidewire carrier defining a lumen configured to receive the guidewire therethrough, the guidewire carrier defining a non-linear resting state, wherein the slider channel is configured to receive the guidewire carrier and transition the guidewire carrier from the non-linear resting state to a linear extended state as the guidewire advancement assembly transitions from the proximal position to the distal position, and wherein the guidewire advancement assembly in the distal position maintains as entirety of the guidewire carrier in the linear extended state.

2. The system according to claim 1, wherein the non-linear resting state includes one of a serpentine coil shape, a coiled shape, a folded shape, or a helical shape.

3. The system according to claim 1, wherein the guidewire carrier is biased to the non-linear resting state and is formed of one of a plastic, a polymer, an elastomer, a rubber, a silicone, a metal, an alloy, or nitinol.

4. The system according to claim 1, wherein the non-linear resting state includes one or more coils extending perpendicular from a longitudinal axis, and wherein a longitudinal length of the slider is greater than a longitudinal length of a coil of the one or more coils.

5. The system according to claim 1, wherein a first distance ("a") that is traveled by the slider as the guidewire advancement assembly transitions between the proximal position and the distal position, is less than a second distance ("b") that is traveled by a tip of the guidewire as the guidewire carrier transitions between the non-linear resting state and the linear extended state.

6. The system according to claim 5, wherein a ratio between the first distance ("a") and the second distance ("b") is expressed as:

$$= \pi \sqrt{\frac{a^2 + b^2}{2}}.$$

7. The system according to claim 1, wherein the guidewire carrier defines a substantially circular cross-sectional shape and includes a left rail and a right rail extending laterally therefrom.

8. The system according to claim 7, wherein the slider channel defines a left recess configured to engage the left rail of the guidewire carrier, and defines a right recess configured to engage the right rail of the guidewire carrier.

9. The system according to claim 1, wherein the guidewire carrier engages the slider channel in a friction fit engagement.

10. The system according to claim 1, wherein one of the guidewire carrier and the guidewire is coupled to a proximal end of the insertion tool.

11. The system according to claim 1, wherein one of a proximal end of the guidewire carrier or a proximal end of the guidewire remains in a longitudinally fixed position relative to the insertion tool.

12. A method of extending a guidewire from an insertion tool, comprising:
  providing a guidewire advancement assembly transitionable between a proximal position and a distal position, and comprising:
    a slider defining a channel; and
    a guidewire carrier engaged with the channel of the slider, and defining a lumen configured to receive the guidewire therein, the guidewire carrier biased to a non-linear resting state;
  advancing the guidewire advancement assembly from the proximal position to the distal position;
  sliding the slider along an outer surface of the guidewire carrier;
  transitioning the guidewire carrier from the non-linear resting state to an extended state, the guidewire advancement assembly in the distal position maintaining an entirety of the guidewire carrier in a linear extended state; and
  advancing a tip of the guidewire in a distal direction.

13. The method according to claim 12, wherein the non-linear resting state includes one of a serpentine coil shape, a coiled shape, a folded shape, or a helical shape.

14. The method according to claim 12, wherein the guidewire carrier is elastically deformable and includes one of a plastic, a polymer, an elastomer, a rubber, a silicone, a metal, an alloy, or a nitinol material.

15. The method according to claim 12, wherein a first distance ("a") that is traveled by the slider as the guidewire advancement assembly transitions between the proximal position and the distal position, is less than a second distance ("b") that is traveled by the tip of the guidewire.

16. The method according to claim 15, wherein a ratio between the first distance ("a") and the second distance ("b") is expressed as:

$$= \pi \sqrt{\frac{a^2 + b^2}{2}}.$$

17. The method according to claim 12, wherein the guidewire carrier defines a substantially circular cross-sectional shape and includes a left rail and a right rail extending laterally therefrom.

18. The method according to claim 17, wherein the channel of the slider defines a left recess configured to engage the left rail of the guidewire carrier, and defines a right recess configured to engage the right rail of the guidewire carrier.

19. The method according to claim 12, wherein the guidewire carrier engages the channel of the slider in a friction fit engagement.

20. The method according to claim 12, wherein one of the guidewire carrier and the guidewire is coupled to a proximal end of the insertion tool.

21. The method according to claim 12, wherein a proximal end of the guidewire carrier or a proximal end of the guidewire remains in a longitudinally fixed position relative to the insertion tool.

* * * * *